United States Patent [19]

Engel

[11] 4,157,397

[45] Jun. 5, 1979

[54] INSECTICIDAL (β-PHENYLVINYL)CYCLOPROPANECARBOXYLATES

[75] Inventor: John F. Engel, Medina, N.Y.

[73] Assignee: FMC Corporation, Philadelphia, Pa.

[21] Appl. No.: 718,254

[22] Filed: Aug. 27, 1976

[51] Int. Cl.$^2$ .................... C07C 69/76; C07C 121/64; A01N 9/24
[52] U.S. Cl. ................... 424/274; 260/465 D; 542/426; 542/429; 560/8; 562/405; 424/282; 424/285; 424/304; 424/308
[58] Field of Search ............... 260/469, 240 R, 468 H, 260/465 D; 560/8; 542/426, 429; 424/274, 282, 285, 304, 308, 309

[56] References Cited

U.S. PATENT DOCUMENTS

| 3,723,649 | 3/1973 | Martel | 260/468 H |
|---|---|---|---|
| 3,786,052 | 1/1974 | Martel et al. | 260/468 H |
| 4,024,163 | 5/1977 | Elliott et al. | 560/8 |

FOREIGN PATENT DOCUMENTS 1580474  9/1969  France .................... 260/468 H

OTHER PUBLICATIONS

Ito et al., J. Org. Chem. 39, No. 12 (1974) pp. 1763–1765.

*Primary Examiner*—Jane S. Myers
*Attorney, Agent, or Firm*—Robert M. Kennedy; H. R. Ertelt

[57] ABSTRACT

New insecticidal (β-phenylvinyl)cyclopropanecarboxylates are described, and their preparation and insecticidal utility are exemplified.

8 Claims, No Drawings

INSECTICIDAL (β-PHENYLVINYL)CYCLOPROPANECARBOXYLATES

This invention relates to the general field of insecticides, particularly to insecticides for use in agriculture to protect crops and animals, but also for household and insecticidal use. The active compounds of this invention are insecticidal esters of 2,2-dimethyl-3-(β-phenylvinyl)cyclopropanecarboxylic acid.

Ever since the structures of naturally occurring pyrethroids were elucidated, synthetic efforts have been directed toward the preparation of related compounds of enhanced insecticidal activity and improved stability toward air and light. A noteworthy advance in this area was the discovery by Elliott et al of certain highly active compounds remarkably resistant to photooxidative degradation, for example, 3-phenoxybenzyl 3-(β,β-dichlorovinyl)-2,2-dimethylcyclopropanecarboxylate, Nature, 246, 169 (1973), Belgian Pat. Nos. 800,006 and 818,811.

Despite the extensive activity in the field of insecticidal cyclopropanecarboxylates, insecticidal 2,2-dimethyl-3-(β-phenylvinyl)cyclopropanecarboxylates have not been described prior to the present invention.

The compounds of the present invention have the formula:

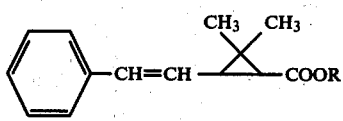

in which R is the residue of an alcohol which in combination with an appropriate acid moiety yields an insecticidal cyclopropanecarboxylate. A wide range of such alcohols are known to the insecticide art. Those R groups useful in compounds of the present invention include:

(1) a benzyl- or phenoxy-substituted benzyl group of the formula:

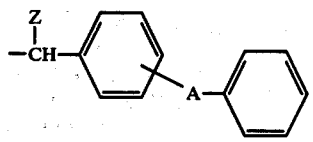

wherein Z is hydrogen, methyl, cyano, ethynyl, or phenyl, and A is —O— or —CH$_2$—;
(2) a benzyl- or phenoxy-substituted furylmethyl group such as 5-benzyl-3-furylmethyl;
(3) an imidomethyl group such as maleimidomethyl, phthalimidomethyl, and tetrahydrophthalimidomethyl;
(4) a benzyl group substituted in at least two ring positions with chloro, methyl, or methylenedioxy groups, for example 3,4-methylenedioxybenzyl, 2-chloro-4,5-methylenedioxybenzyl, and 2,4-dimethylbenzyl;
(5) a substituted cyclopentenonyl group such as allethrolonyl.

The more readily available R groups which give active insecticides of the present invention are 3-phenoxybenzyl, α-cyano-3-phenoxybenzyl, and 5-benzyl-3-furylmethyl.

The preparation and insecticidal properties of the compounds of this invention are illustrated in the following specific examples. Unless otherwise specified, all temperatures are in degrees centigrade, and concentration of liquid volume was carried out under the reduced pressure produced by a water aspirator.

EXAMPLE 1

Synthesis of 3-Phenoxybenzyl 2,2-Dimethyl-3-(β-phenylvinyl)-cyclopropanecarboxylate

A. Preparation of Ethyl 2,2-dimethyl-3-(β-phenylvinyl)-cyclopropanecarboxylate Under a nitrogen atmosphere and anhydrous conditions 43 ml of an approximately 2.5 M solution of n-butyllithium in hexane was added to a suspension of 41.81 g benzyltriphenylphosphonium chloride in 200 ml anhydrous benzene. During the addition of the n-butyllithium solution in small portions the reaction temperature was maintained at about 25° by intermitent cooling with an ice-water bath. After addition of the n-butyllithium solution was completed, the reaction mixture was stirred at room temperature for 2.75 hours. The reaction mixture was then added, in 10–20 ml portions via a glass tube, to an anhydrous, ice cold, stirred solution of 16.7 g ethyl caronaldehyde in 50 ml of benzene. During the addition, the reaction mixture was cooled with an ice-water bath. The reaction mixture was allowed to warm to room temperature over a period of 0.5 hr and then stirred for an additional hour. The reaction mixture was filtered, and the filtrate was washed sequentially with two 200 ml portions of water and two 100 ml portions of saturated brine and then dried over anhydrous magnesium sulphate. The solvent was removed and the residue dried under reduced pressure to yield 27.71 g amorphous white solid. The solid was triturated with 150 ml anhydrous hexane, filtered and concentrated to yield 20.59 g of viscous liquid. The nmr and ir spectra were consistent with the expected mixture of geometric isomers of ethyl 2,2-dimethyl-3-(β-phenylvinyl)cyclopropanecarboxylate.

B. Preparation of 2,2-dimethyl-3-(β-phenylvinyl)-cyclopropanecarboxylic acid A mixture of 30.68 g of ethyl 2,2-dimethyl-3-(β-phenylvinyl)cyclopropanecarboxylate, 5 g of sodium hydroxide, 29 ml of ethanol and 300 ml of water was heated at 50° for 35 hours. After standing at room temperature for 12 hours, the reaction mixture was concentrated under reduced pressure. The concentration was diluted with 450 ml of dry benzene, then taken to dryness under reduced pressure. The residue was shaken with a mixture containing 400 ml of water and 100 ml saturated brine, and the resulting mixture was then extracted with chloroform. The aqueous phase was made acidic (pH 3) with 320 ml of 3% hydrochloric acid and extracted with a 500 ml portion of diethyl ether followed by two 1200 ml portions of diethyl ether. The ethereal extracts were washed with four 300 ml portions of water and then dried over anhydrous magnesium chloride. The dried ethereal solution was filtered and the solvent stripped to yield 22.34 g of 2,2-dimethyl-3-(β-phenylvinyl)cyclopropanecarboxylic acid. The nmr and ir spectra were consistent with the expected isomeric mixture.

C. Preparation of 3-phenoxybenzyl 2,2-dimethyl-3-(β-phenylvinyl)cyclopropanecarboxylate To a stirred mixture of 6.10 g of 2,2-dimethyl-3-(β-phenylvinyl)cyclopropanecarboxylic acid in 50 ml of dry benzene, under a nitrogen gas atmosphere and at 25°, was added 1.2 ml of pyridine (4.0% excess), then 1.1 ml of thionyl chloride (7.0% excess). The exothermic reaction caused the reaction mixture temperature to rise to 35°–40°. A copious amount of white pyridine hydrochloride precipitated from the reaction mixture. Stirring at ambient temperature was continued for 7 hours. To the above suspension containing 2,2-dimethyl-3-(2-phenylvinyl)cyclopropanecarbonyl chloride and pyridine hydrochloride was added 1.7 ml of pyridine and 100 ml of dry benzene; then, with stirring, 3.07 grams (7.0% excess) of 3-phenoxybenzyl alcohol in 50 ml of dry benzene. The reaction mixture was stirred at ambient temperature for 13.3 hours. Thin layer chromatographic analysis of the reaction mixture indicated the reaction was complete. The reaction mixture was filtered, and the filtrate was concentrated, diluted with hexane, and refiltered. The filtrate was concentrated under reduced pressure to a pale yellow oil and then further concentrated by use of a vacuum pump. The oil was dissolved in 30 ml diethyl ether and washed with two 700 ml portions of water. The ether layer was washed with a saturated brine solution, then dried over magnesium sulfate. The mixture was filtered and the filtrate evaporated to a residual 5.66 g of oil. The oil was filtered through a column containing 51 g of silica gel and with pentane and pentane-ether as eluent to give 4.1 g (72%) of 3-phenoxybenzyl 2,2-dimethyl-3-(β-phenylvinyl)cyclopropanecarboxylate. The nmr and the ir spectra were consistent with the proposed structure.

Analyses calc'd for $C_{27}H_{26}O_3$: C 81.38; H, 6.58: Found: C 81.30; H 6.59.

d. Separation of Isomers

A sample of 3-phenoxybenzyl 2,2-dimethyl-3-(β-phenylvinyl)cyclopropanecarboxylate was separated into three isomers by use of a medium pressure liquid chromatographic unit. The separation, with 50 parts hexane, 1 part ethyl acetate as eluent, was carried out on a silica gel column and gave sixty 25 ml fractions. Fractions 24–27 were combined and evaporated under reduced pressure to give 0.40 g of 3-phenoxybenzyl 2,2-dimethyl-cis-3-(β-(Z)-phenylvinyl)cyclopropanecarboxylate. In the same manner, fractions 30–37 were combined to give 0.94 g of 3-phenoxybenzyl 2,2-dimethyl-trans-3-(β-(E)-phenylvinyl)cyclopropanecarboxylate. Fractions 28–29 were combined to give 0.25 g of 3-phenoxybenzyl 2,2-dimethyl-trans 3-(β-(Z)-phenylvinyl)cyclopropanecarboxylate. The nmr and ir spectra were consistent with the structure assigned to each isomer.

The structure assignments of the isomers were based on the following nmr data in which d means doublet, dd means doublet of doublet, and m means multiplet. Tetramethylsilane was used as an internal standard. Values reported are ppm for deuterated chloroform solutions. $H_1$ and $H_3$ are respectively on the 1- and 3- carbons of the cyclopropane ring, and $H_\alpha$ and $H_\beta$ are respectively on the vinyl group α and β to the cyclopropane ring.

|  | trans (E) | cis (Z) | trans (Z) |
|---|---|---|---|
| $H_1$ | d, 1.73 |  | d, 1.60 |
|  |  | m 1.70–2.32 |  |
| $H_3$ | dd, 2.21 |  | dd, 2.43 |
| $H_\alpha$ | dd, 5.90 | dd, 5.96 | dd, 5.40 |
| $H_\beta$ | d, 6.50 | d, 6.58 | d, 6.57 |
| $J_{H_\alpha - H_\beta}$ | 16 Hz | 11 Hz | 11 Hz |

By the methods exemplified above may be prepared other insecticidal esters of 2,2-dimethyl-3-(β-phenylvinyl)cyclopropanecarboxylic acid such as α-cyano-3-phenoxybenzyl 2,2-dimethyl-3-(β-phenylvinyl)cyclopropanecarboxylate and 5-benzyl-3-furylmethyl 2,2-dimethyl-3-(β-phenylvinyl)cyclopropanecarboxylate.

EXAMPLE 2

Toxicity to Insects and Mites

Initial Contact Activity: One quarter gram of test compound was dissolved in 20 ml of acetone and this solution was dispersed in 180 ml of water containing one drop of isooctylphenyl polyethoxyethanol. Aliquots of this solution, which corresponds to 1250 ppm of active ingredient, were diluted with an appropriate amount of water to provide solutions containing 312 ppm or 156 ppm of active ingredient. Test organisms and techniques were as follows: the activities against the Mexican bean beetle (*Epilachna varivestis* Muls.) and the southern armyworm (*Spodoptera eridania* [Cram.]) were evaluated by dipping the leaves of pinto bean plants into the test solution and infesting the leaves with the appropriate immature-form insects when the foliage had dried; the activity against the pea aphid (*Acyrthosiphon pisum* [Harris]) was evaluated on broad bean plants whose leaves were dipped before infestation with adult aphids; the activity against two-spotted spider mites (*Tetranychus urticae* Koch) was evaluated on pinto bean plants whose leaves were dipped after infestation with adult mites; the activities against the milkweed bug (*Oncopeltus fasciatus* [Dallas]), and the plum curculio (*Conotrachelus nenuphar* [Herbst]) were evaluated by spraying the test solutions into glass dishes or jars containing the adult insects; the activities against the confused flour beetle (*Tribolium confusum* [duVal]) and granary weevil [*Sitophilus granarius* (Linnaeus)] were evaluated by introducing the insects into glass dishes which had been previously sprayed with test solution and allowed to dry. All organisms in the test were maintained in a holding room at 80° F. and 50% relative humidity for an exposure period of 48 hours (96 hours for the confused flour beetle). At the end of this time, the dead and living insects or mites were counted, and the percent kill was calculated. Results of these tests are summarized in Table 1. While all the isomers tested show insecticidal activity, the cis(Z) isomer appears the most active against most test species. Residual Contact Activity: The residual contact activity of the compounds was determined on the same organisms using the techniques described above, except that in each case the treated surface was allowed to dry and was exposed to normal light and air for seven days before introduction of the mites or insects. Results of these tests are summarized in Table 2. Again, the cis(Z) isomer appears the most active of the isomers tested.

It is anticipated that, in the normal use of the compounds of the present invention as insecticides, the compounds will usually not be employed free from admixture or dilution, but will ordinarily be used in a suitable formulated state compatible with the method of application. The insecticidal cyclopropanecarboxylates of this invention may be formulated with the usual additives and extenders used in the preparation of pesticidal compositions. The toxicants of this invention, like most pesticidal agents, are incorporated with the adjuvants and carriers normally employed for facilitating the dispersion of active ingredients, recognizing the accepted fact that the formulation and mode of application of a toxicant may affect the activity of the material. The present compounds may be applied, for example, as a spray, dust, or granule, to the area in which pest control is desired, the choice of application varying of course with the type of pest and the environment. Thus, the compounds of this invention may be formulated as granules of large particle size, as powdery dusts, as wettable powders, as emulsifiable concentrates, as solutions, and the like.

Dusts are admixtures of the active ingredients with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as dispersants and carriers for the toxicant. These finely divided solids have an average particle size of less than about 50 microns. A typical dust formulation useful herein contains 10.0 parts of 3-phenoxybenzyl 2,2-dimethyl-3-($\beta$-phenylvinyl)cyclopropanecarboxylate, 30.0 parts of bentonite clay, and 60.0 parts of talc.

The compounds of the present invention may be made into liquid concentrates by solution or emulsion in suitable liquids, and into solid concentrates by admixtures with talc, clays, and other known solid carriers used in the pesticide art. The concentrates are compositions containing about 5-50% toxicant, and 95-50% inert material which includes dispersing agents, emulsifying agents, and wetting agents. The concentrates are diluted for practical application, with water or other liquid for sprays or with additional solid carrier for use as dusts. Typical carriers for solid concentrates (also called wettable powders) include fuller's earth, kaolin clays, silicas, and other highly absorbent, readily wet inorganic diluents. A solid concentrate formulation useful herein contains 1.5 parts each of sodium lignosulfonate and sodium laurylsulfate as wetting agents, 25.0 parts of 3-phenoxybenzyl 2,2-dimethyl-3-($\beta$-phenylvinyl)cyclopropanecarboxylate and 72.0 parts of bentonite clay.

Useful liquid concentrates include the emulsifiable concentrates, which are homogeneous liquid or paste compositions readily dispersed in water or other dispersant, and may consist entirely of the toxicant with a liquid or solid emulsifying agent, or may also contain a liquid carrier such as xylene, heavy aromatic naphthas, isophorone and other nonvolatile organic solvents. For application, these concentrates are dispersed in water or other liquid carrier, and normally applied as a spray to the area to be treated.

Typical wetting, dispersing or emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1-15% by weight of the pesticidal composition.

Other useful formulations include simple solutions of the active ingredient in a solvent in which it is completely soluble at the desired concentration, such as acetone or other organic solvents.

The concentration of the toxicant in the dilution generally used for application is normally in the range of about 2% to about 0.001%. Many variations of spraying and dusting compositions in the art may be used, by substituting a compound of this invention into compositions known or apparent to the art.

Pesticidal compositions may be formulated and applied with other active ingredients, including other insecticides, nematicides, acaricides, fungicides, plant growth regulators, fertilizers, etc. In applying the chemicals, it is obvious that an effective amount and concentration of the compound of the invention should be employed. For agricultural application the active ingredient of the invention may be applied at a rate of 75 to 4,000 g per hectare, preferably 150 to 3,000 g per hectare.

It is apparent that many modifications may be made in the structure, preparation, formulation and application of the compounds of this invention, without departing from the spirit and scope of the invention and of the following claims.

Table 1

| Compound of Example 1 | Conc. (PPM) | Initial Toxicity to Insects and Mites % Kill | | | | | | | |
|---|---|---|---|---|---|---|---|---|---|
| | | BB | AW | PA | M | MWB | PC | FB | GW |
| Isomer Mixture | 1250 | 100 | 100 | 100 | 70 | 100 | ND | ND | 89 |
| (as prepared) | 312 | 100 | 100 | 93 | 25 | 4 | ND | ND | 25 |
| Trans (E) | 1250 | 100 | 100 | 60 | 2.5 | 100 | 30 | 0 | 35 |
| | 312 | 18* | 100* | 0* | 5 | 85 | 0 | 0 | 40 |
| Trans (Z) | 1250 | 71 | 100 | 95 | 16 | 100 | 0 | 0 | 15 |
| | 312 | 94* | 60* | 6* | 4.2 | 60 | 10 | 0 | 2.5 |
| Cis (Z) | 1250 | 100 | 100 | 100 | 0.3 | 100 | 81 | 0 | 65 |

Table 1-continued

| Compound of Example 1 | Conc. (PPM) | Initial Toxicity to Insects and Mites % Kill | | | | | | | |
|---|---|---|---|---|---|---|---|---|---|
| | | BB | AW | PA | M | MWB | PC | FB | GW |
| | 312 | 100* | 100* | 50* | 7.4 | 100 | 10 | 0 | 30 |

*at 156 ppm
BB: Mexican bean beetle
AW: Southern army worm
PA: Pea aphid
M: Two-spotted spider mite
GW: Granary weevil
MWB: Milkweed bug
PC: Plum curculio
FB: Confused flour beetle
ND: No data

Table 2

| Compound of Example 1 | Conc. (PPM) | Residual (7-day) Toxicity to Insects and Mites % Kill | | | | | | | |
|---|---|---|---|---|---|---|---|---|---|
| | | BB | AW | PA | M | MWB | PC | FB | GW |
| Isomer Mixture | 1250 | 93 | 100 | 100 | 0 | 15 | ND | ND | 12 |
| (as prepared) | 312 | 100 | 57 | 94 | 0 | 36 | ND | ND | 10 |
| Trans (E) | 1250 | 20 | 15 | 0 | 0 | 10 | 0 | 30 | 0 |
| | 312 | 0* | 57 | 30 | ND | 5 | 0 | 18 | 0 |
| Trans (Z) | 1250 | 50 | 0 | 30 | 0 | 0 | 5 | 10 | 5 |
| | 312 | 29* | 0 | 0 | ND | 10 | 0 | 35 | 0 |
| Cis (Z) | 1250 | 100 | 100 | 80 | 0 | 50 | 0 | 13 | 53 |
| | 312 | 92* | 50 | ND | 10 | 0 | 20 | 13 | |

*at 156 ppm
BB: Mexican bean beetle
AW: Southern army worm
PA: Pea aphid
M: Two-spotted spider mite
GW: Granary weevil
MWB: Milkweed bug
PC: Plum curculio
FB: Confused flour beetle
ND: No data

I claim:

1. An insecticidal compound of the formula:

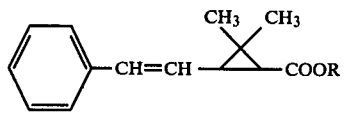

in which R is an alcohol residue selected from the group consisting of:
(a) a benzyl- or phenoxy-substituted benzyl group of the formula:

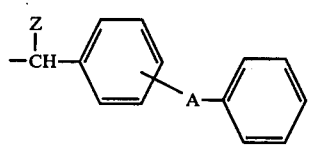

wherein Z is hydrogen, methyl, cyano, ethynyl, or phenyl, and Z is —O— or —CH$_2$—;
(b) a benzyl- or phenoxy-substituted furylmethyl group;
(c) an imidomethyl group selected from the group consisting of maleimidomethyl, phthalimidomethyl, and tetrahydrophthalimidomethyl; and
(d) a benzyl group substituted in at least two ring positions with chloro, methyl, or methylenedioxy group.

2. A compound of claim 1 in which R is 3-phenoxybenzyl, α-cyano-3-phenoxybenzyl, or 5-benzyl-3-furylmethyl.

3. The compound of claim 2 which is 3-phenoxybenzyl 2,2-dimethyl-3-(β-phenylvinyl)cyclopropanecarboxylate.

4. The compound of claim 3 in which the predominant isomer is the cis (Z) form.

5. The insecticidal compound of claim 1 in which R is an alcohol residue selected from the group consisting of:
(a) a benzyl-or phenoxy-substituted benzyl group of the formula:

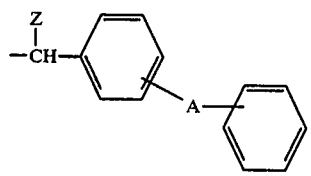

wherein Z is hydrogen, methyl, cyano, ethynyl, or phenyl and A is —O— or —CH$_2$—;
(b) 5-benzyl-3-furylmethyl;
(c) an imidomethyl group selected from the group consisting of maleimidomethyl, phthalimidomethyl, and tetrahydrophthalimidomethyl;
(d) a benzyl group substituted in at least two ring positions with chloro, methyl, or methylenedioxy groups, selected from the group consisting of 3,4-methylenedioxybenzyl, 2-chloro-4,5-methylenedioxybenzyl, and 2,4-dimethylbenzyl.

6. An insecticidal composition comprising an insecticidally effective amount of a compound of claim 1 in admixture with an agriculturally acceptable extender.

7. An insecticidal composition of claim 6 which contains a surface active agent.

8. A method of controlling insects which comprises applying to the locus where control is desired an insecticidally effective amount of a compound of claim 1.

* * * * *